US012796901B2

(12) United States Patent
Shelton et al.

(10) Patent No.: US 12,796,901 B2
(45) Date of Patent: Nov. 17, 2026

(54) SYSTEM FOR MULTIMODAL APPROACH TO COMPUTER ASSISTED DIAGNOSIS OF OTITIS MEDIA AND METHODS OF USE

(71) Applicant: PhotoniCare Inc., Durham, NC (US)

(72) Inventors: Ryan Shelton, Bentonville, AR (US); Ryan Nolan, Chapel Hill, NC (US); Nishant Mohan, Raleigh, NC (US)

(73) Assignee: PhotoniCare Inc., Durham, NC (US)

( * ) Notice: Subject to any disclaimer, the term of this patent is extended or adjusted under 35 U.S.C. 154(b) by 261 days.

(21) Appl. No.: 18/420,056

(22) Filed: Jan. 23, 2024

(65) Prior Publication Data

US 2024/0225436 A1 Jul. 11, 2024

Related U.S. Application Data

(63) Continuation of application No. PCT/US2022/038148, filed on Jul. 25, 2022.

(60) Provisional application No. 63/225,129, filed on Jul. 23, 2021.

(51) Int. Cl.

| | |
|---|---|
| ***A61B 1/227*** | (2006.01) |
| ***A61B 1/00*** | (2006.01) |
| ***A61B 5/00*** | (2006.01) |
| ***G06V 10/82*** | (2022.01) |
| ***G16H 50/20*** | (2018.01) |

(52) U.S. Cl.

CPC ............ *A61B 1/227* (2013.01); *A61B 5/0066* (2013.01); *G06V 10/82* (2022.01); *G16H 50/20* (2018.01); *A61B 1/00* (2013.01)

(58) Field of Classification Search

CPC . A61B 1/000096; A61B 1/227; A61B 5/0066; A61B 5/6817; A61B 5/7264; A61B 5/7267; A61B 1/00; G01B 9/02091; G16H 50/20; G06V 10/82

USPC .......................................................... 382/128

See application file for complete search history.

(56) References Cited

U.S. PATENT DOCUMENTS

| | | | | |
|---|---|---|---|---|
| 9,867,528 B1 | 1/2018 | Boppart et al. | |
| 2016/0007840 A1* | 1/2016 | Boppart ............... | A61B 5/6817 600/188 |
| 2018/0156599 A1 | 6/2018 | Boppart et al. | |
| 2019/0343390 A1* | 11/2019 | Boppart ................. | A61B 1/227 |
| 2020/0037930 A1* | 2/2020 | Abramoff ............ | A61B 5/0066 |
| 2020/0286227 A1* | 9/2020 | Corredor .............. | A61B 8/5223 |
| 2022/0261987 A1* | 8/2022 | Gurcan .................. | G06V 10/82 |

FOREIGN PATENT DOCUMENTS

| | | |
|---|---|---|
| CN | 110796249 A | 2/2020 |
| JP | 2014-510583 A | 5/2014 |
| JP | 2014-532511 A | 12/2014 |

(Continued)

OTHER PUBLICATIONS

European Patent Office, European Search Report and Opinion issued in corresponding application EP Application No. 22846722.1 dated May 6, 2025, 12 pages.

(Continued)

*Primary Examiner* — Kenny A Cese

(74) *Attorney, Agent, or Firm* — J. Peter Paredes; Amin Wasserman Gurnani LLP

(57) ABSTRACT

Provided herein are systems, methods, and apparatuses for diagnosing otitis media and related conditions using multiple sensing and imaging technologies.

13 Claims, 11 Drawing Sheets

(56) References Cited

FOREIGN PATENT DOCUMENTS

| | | | |
|---|---|---|---|
| JP | 2019519024 | A | 7/2019 |
| KR | 20180027976 | A | 3/2018 |
| WO | 2020/023527 | A1 | 1/2020 |
| WO | 2020/154698 | A1 | 7/2020 |
| WO | 2020/161712 | A1 | 8/2020 |

OTHER PUBLICATIONS

Monroy, G. L., et al., "Non-invasive optical assessment of viscosity of middle ear effusions in otitis media", Journal of Biophotonics, vol. 10, No. 3, Mar. 24, 2016, pp. 394-403.
Monroy, G. L., et al., "Noninvasive Depth-Resolved Optical Measurements of the Tympanic Membrane and Middle Ear for Differentiating Otitis Media: Differentiation of Otitis Media Using OCT", The Laryngoscope, vol. 125, No. 8, Aug. 1, 2015, pp. E276-E282.
Monroy, G. L., et al., "Automated classification platform for the identification of otitis media using optical coherence tomography", npj Digital Medicine, vol. 2, No. 1, Dec. 1, 2019, 11 pages.
WIPO/ISA/US, International Search Report and Written Opinion for corresponding application PCT/US2022/038148 dated Oct. 25, 2022, 9 pages.
Japanese Patent Office, Office Action issued in corresponding application JP2024-503929 dated Jul. 21, 2026, 6 pages.

* cited by examiner

FIG. 1B
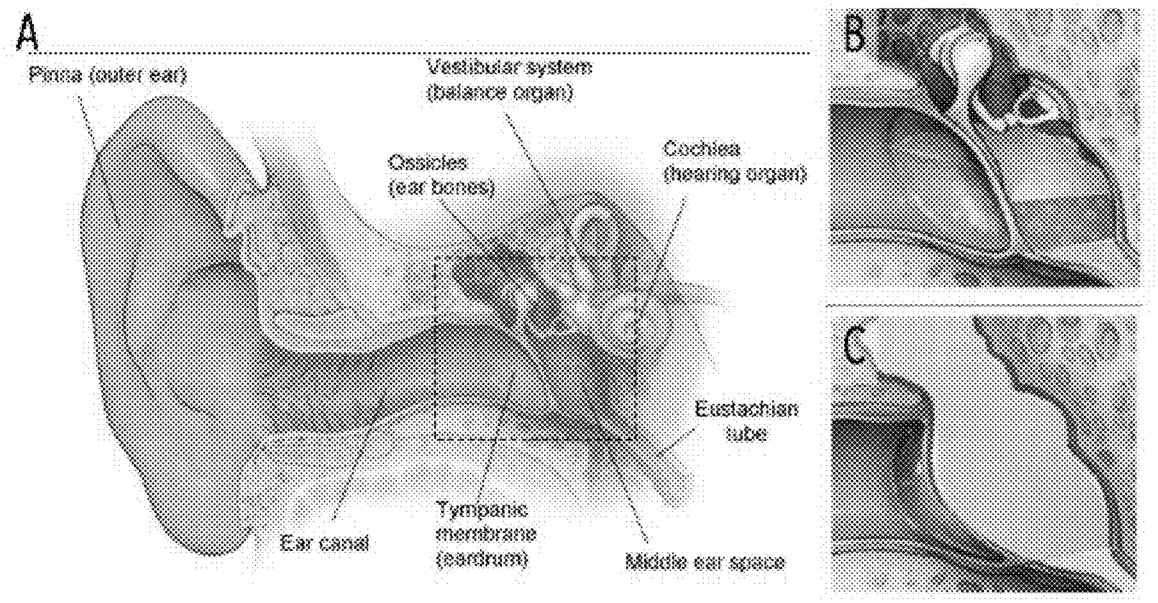
FIG. 1A
FIG. 1C
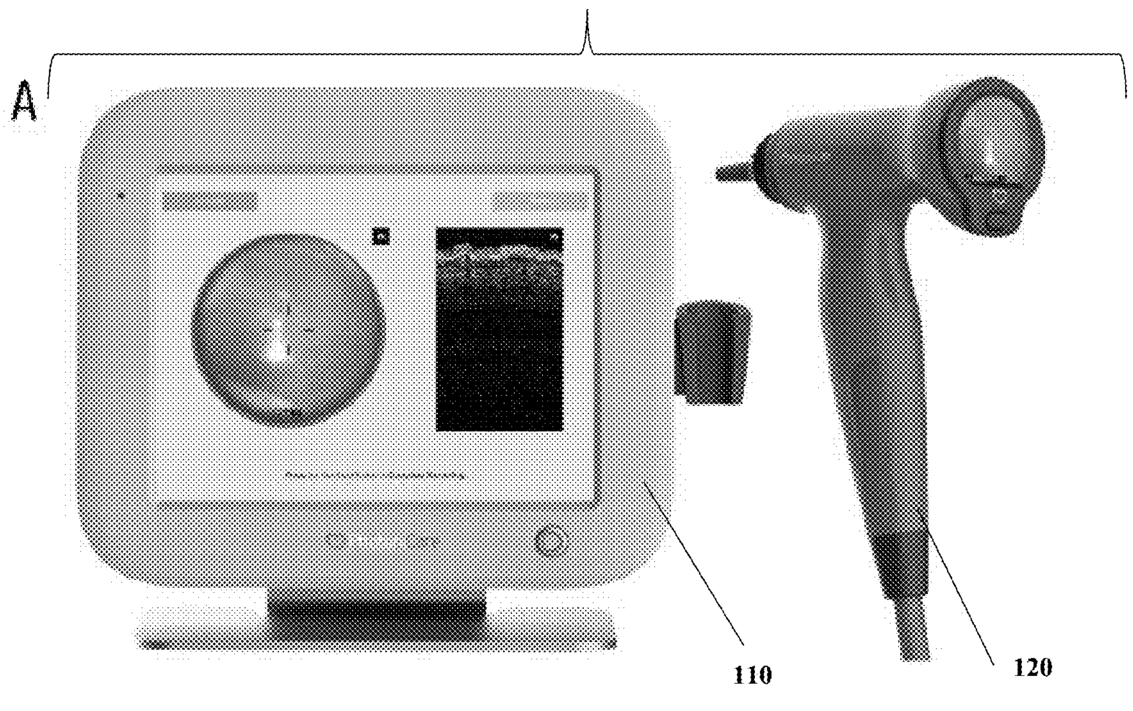
FIG. 2A

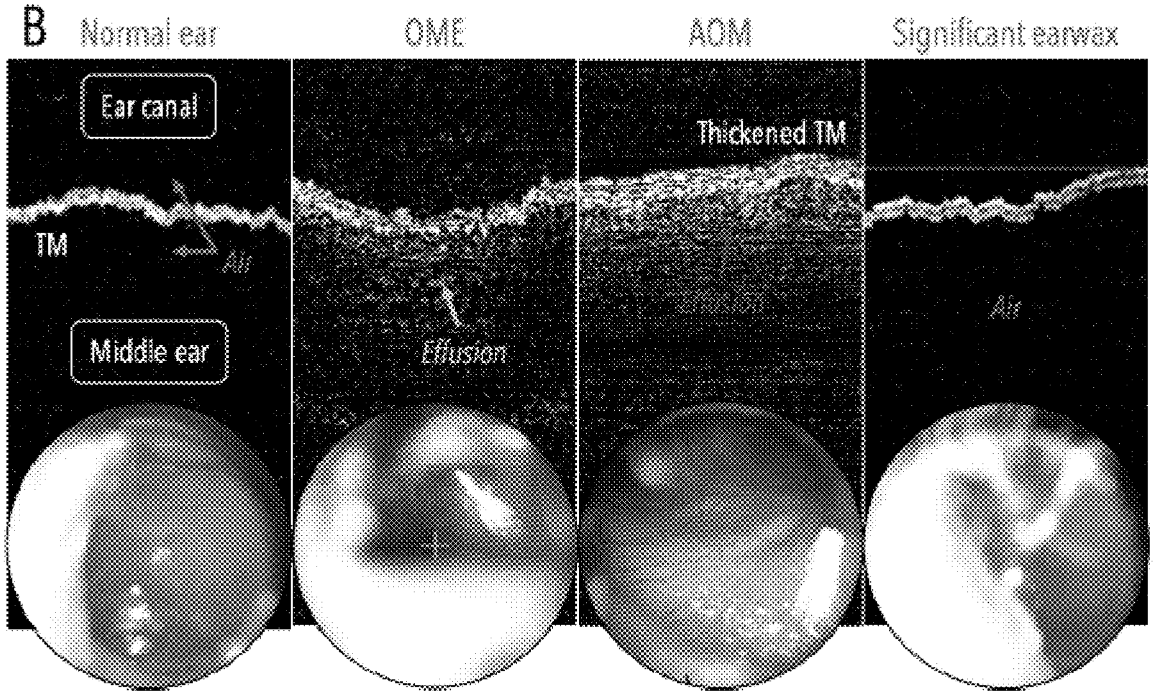
FIG. 3A FIG. 3B FIG. 3C FIG. 3D
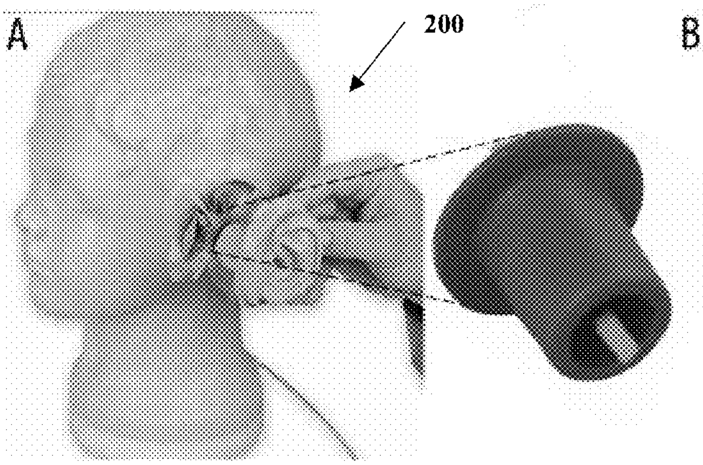
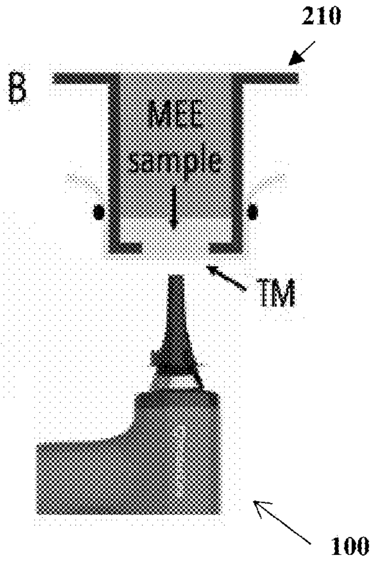
FIG. 4A
FIG. 4B

SYSTEM FOR MULTIMODAL APPROACH TO COMPUTER ASSISTED DIAGNOSIS OF OTITIS MEDIA AND METHODS OF USE

CROSS-REFERENCE TO RELATED APPLICATIONS

The present application claims priority to PCT application serial no. PCT/US2022/038148 filed Jul. 25, 2022, which claims priority to U.S. provisional application Ser. No. 63/225,129, filed Jul. 23, 2021, each herein incorporated by reference in their entireties.

BACKGROUND

The invention generally relates to otitis media and related conditions.

Otitis media or the infection of the middle ear is one of the leading causes for children to visit their healthcare providers. The middle ear infection results in the presence of fluid behind the eardrum that presses against the eardrum resulting in acute pain. The diagnosis of whether the pain is resulting from the infection behind the eardrum is often made by observing the eardrum using an otoscope, a device that provides a magnified view of the eardrum. Recently, new methods have been developed to provide the state of the middle ear behind the eardrum directly.

The present invention attempts to solve these problems, as well as others.

SUMMARY OF THE INVENTION

Provided herein are systems, methods and apparatuses for diagnosing otitis media and related conditions using multiple sensing and imaging technologies.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

BRIEF DESCRIPTION OF THE DRAWINGS

In the accompanying figures, like elements are identified by like reference numerals among the several preferred embodiments of the present invention.

FIG. 1A is a cross-sectional schematic image of a normal, healthy ear, the middle ear space just behind the tympanic membrane (eardrum) is filled with air. FIG. 1B is a cross-sectional schematic image of the swelling of the eustachian tube can restrict proper middle ear drainage, and the middle ear space can fill up with serous effusion: a clear, watery fluid during otitis media with effusion (OME). FIG. 1C is a cross-sectional schematic image of purulent effusion: a cloudy, viscous fluid during acute otitis media (AOM).

FIG. 2A is a front perspective view of the OCT system and scope.

FIG. 3A is an OCT image (top) and an otoscope image (bottom) of a normal, healthy ears, showing the space contains only air (green arrows). FIG. 3B is an OCT image and an otoscope image of in abnormal ears, fluid can build up and the ability to differentiate this fluid as that of OME, wherein clear, watery serous effusion (orange arrow) is present. FIG. 3C is an OCT image and an otoscope image of an abnormal ear showing fluid can build up identified as AOM, wherein cloudy, purulent effusion (red arrow) is present. FIG. 3D is an OCT image and an otoscope image of the middle ear with significant earwax present.

FIG. 4A is a perspective view of an established representative middle ear model complete with TM (porcine intestinal lining) and middle ear cavity (red) and FIG. 4B is a side view of an otoscopy training model loaded with human MEE samples used to collect OCT system and scope data for applying the machine learning model for identification and classification of MEE type, where OCT system and scope imaging was conducted from beneath the ear model to ensure MEE data collection.

FIG. 8A is the original otoscopic image; FIG. 8B is the human annotation of the eardrum; and FIG. 8C is the AI annotation of the eardrum with a dice score of 0.96. Dice score is commonly used for manually annotated and machine segmented examples.

DETAILED DESCRIPTION OF THE INVENTION

Figure 2B:
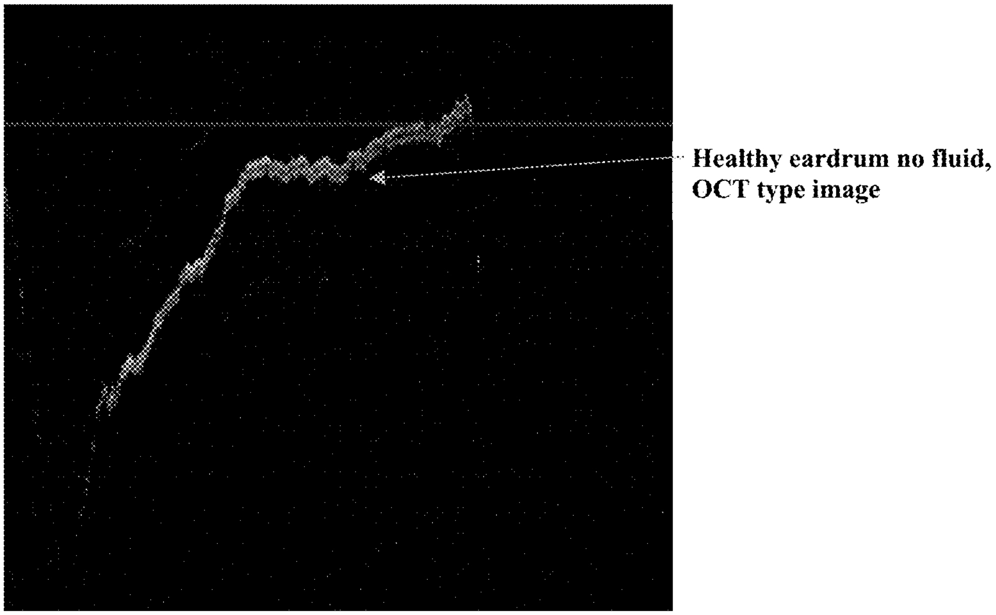
FIG. 2B is an OCT image of the eardrum.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

The words proximal and distal are applied herein to denote specific ends of components of the instrument described herein. A proximal end refers to the end of an instrument nearer to an operator of the instrument when the instrument is being used. A distal end refers to the end of a component further from the operator.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques, and procedures for accomplishing a given task including, but not limited to, those manners, means, techniques, and procedures either known to, or readily developed from known manners, means, techniques and procedures by practitioners of the chemical, pharmacological, biological, biochemical, and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Description

Ear infections are accompanied by middle ear effusion (MEE), or fluid build-up in the middle ear due to impaired eustachian tube drainage, as shown in FIGS. 1A-1C. During acute otitis media (AOM), a cloudy fluid (i.e. purulent effusion) presents, and according to the current American Academy of Pediatrics (AAP) guideline, antimicrobials should be prescribed if, in addition to the MEE present, there is bulging of the TM and a reduction in TM movement under pneumatic otoscopy (currently rarely performed). In otitis media with effusion (OME), clear, watery fluid (i.e. serous effusion) is present in the middle ear space. Per the current American Academy of Otolaryngology-Heads and Neck Surgery (AAO-HNS) guideline, antibiotics are not recommended for OME, and especially not for suspected cases where fluid is actually absent. If the MEE is not resolved over several recurrent acute episodes or a single chronic episode, this fluid can advance to a more viscous state (i.e. mucoid effusion), requiring tympanostomy tube placement (TTP) surgery. FIG. 1A shows in a normal, healthy ear, the middle ear space just behind the tympanic membrane (eardrum) is filled with air. When sick, swelling of the eustachian tube can restrict proper middle ear drainage, and the middle ear space can fill up with serous effusion, as shown in FIG. 1B: a clear, watery fluid during otitis media with effusion (OME) or as shown in FIG. 1C, purulent effusion: a cloudy, viscous fluid during acute otitis media (AOM). The presence of effusion, especially over prolonged periods of time, causes significant hearing loss, which can lead to learning and language developmental delays, and ultimately requires TTP surgery for drainage and aeration.

The present methods disclosed herein support a system for diagnosing otitis media comprising: a method for observing contents behind the eardrum and generating data from the contents behind the eardrum, a method for observing the surface of the eardrum and generating images of the surface of the eardrum, and a computation method using the data from the contents behind the eardrum and the images of the surface of the eardrum to provide a diagnosis of otitis media. The system for observing the contents behind the eardrum uses electromagnetic radiation, low-coherence interferometry, or mechanical waves like ultrasound, according to one embodiment. The system for observing the eardrum surface uses electromagnetic radiation and an electromagnetic detector. The computation method for diagnosing otitis media is based on machine learning including deep learning (neural networks), support vector machines, logistic regression, or random forests. The computational technique for diagnosing otitis media segments the eardrum from the rest of the contents. The surface image is co-registered with the sub-surface information in spatial coordinates. Only the subsurface information is used to detect contents and structures in the middle ear, according to one embodiment. The computational method provides a scale that indicates state of the middle ear from healthy to severely ill. The system diagnoses the type of fluid present behind the eardrum. Fluid types can include serous, mucoid, mucopurulent, and seropurulent.

Figure 2C:
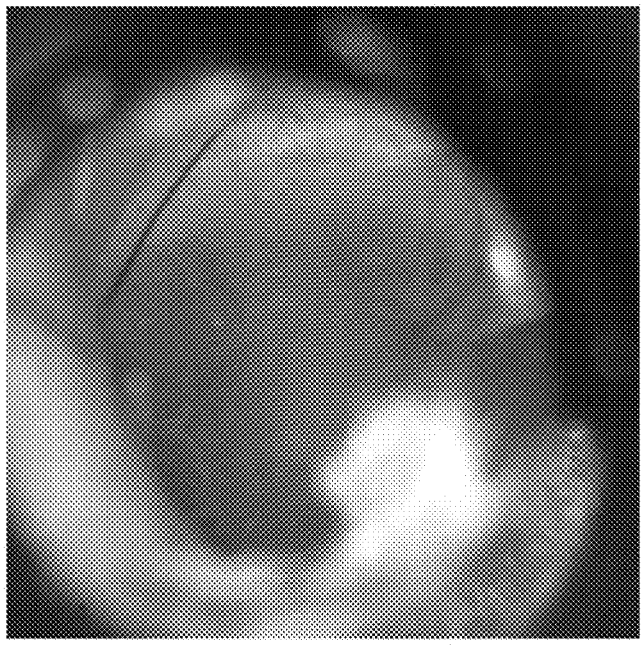
FIG. 2C is an otoscopic image of the eardrum.
Figure 2D:
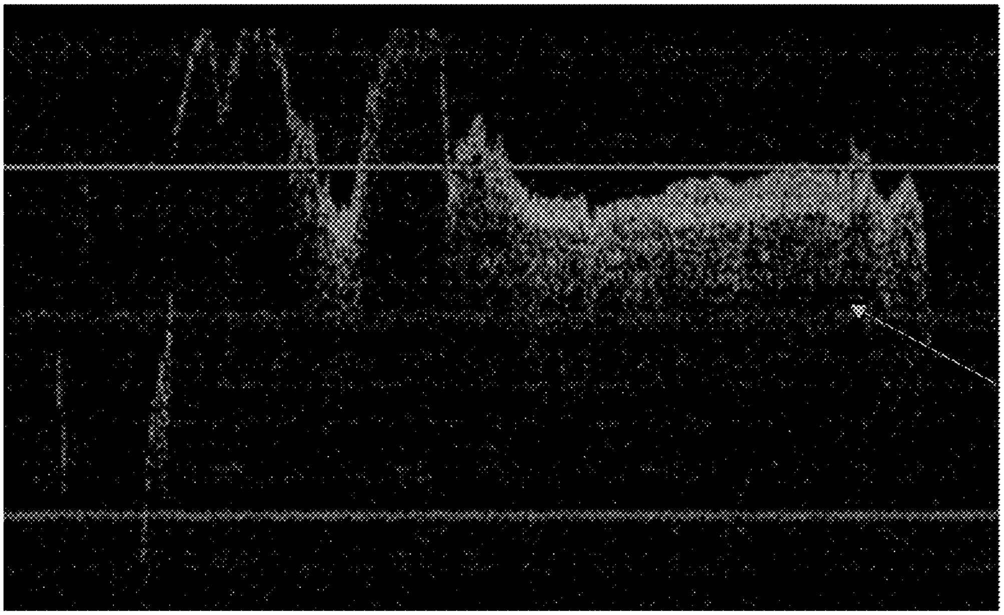
FIG. 2D is the OCT signal acquired on a clear portion of the eardrum unobstructed by the contents of the ear canal and fluid is detected behind the eardrum.
Figure 2E:
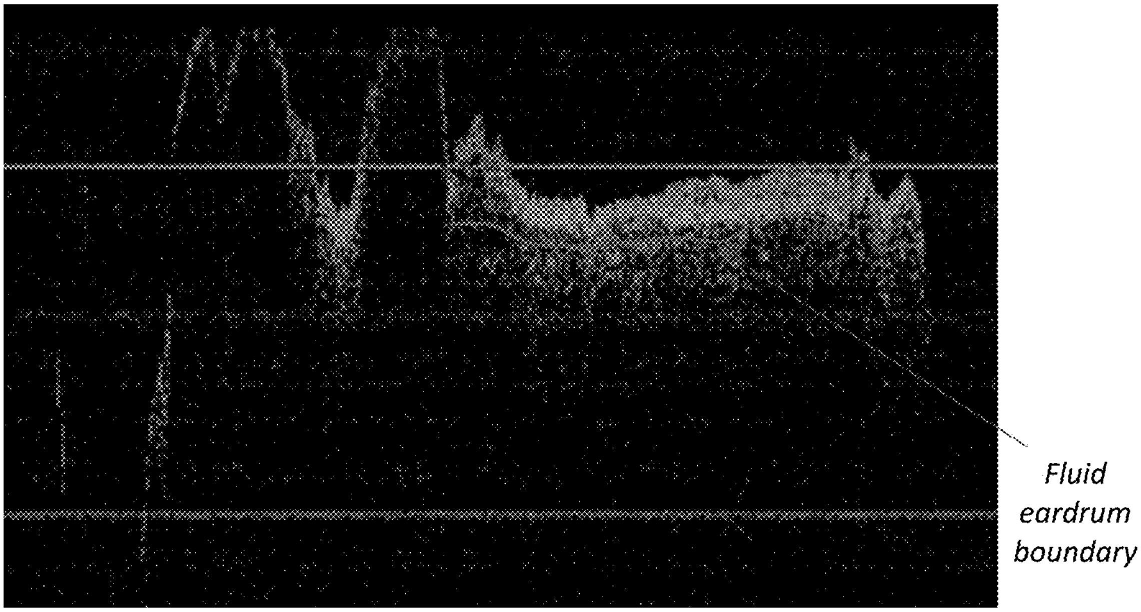
FIG. 2E is the fluid-eardrum boundary in the OCT image.

In one embodiment, the system and method for generating data from the contents behind the ear is an optical coherence tomography (OCT) system and scope 100, as shown in FIG. 2A. The OCT system and scope 100 comprises an OCT system 110 and a scope 120 that interface with the ear in the same way clinicians are accustomed to using an otoscope. In one embodiment, the OCT system is a spectral-domain based OCT platform including OCT architecture. As shown in FIG. 2A, an OCT system 110 maps the subsurface information by estimating time of infrared light using interference of partially coherent light through a scope 110. A diagnostic decision of clinical relevance requires interpreting the content of the images or signals and their relationships to each other. In one embodiment, an otoscopic image of the eardrum is acquired, as shown in FIG. 2C, and co-registered with the OCT image, as shown in FIG. 2B. Diagnosis of otitis media is made if and when OCT signal is acquired on a clear portion of the eardrum unobstructed by the contents of the ear canal and fluid is detected behind the eardrum, as shown in FIG. 2D. The method comprises combining two different modalities, as well as distinguishing signals of eardrum from the fluid. The fluid-eardrum boundary in the OCT image is shown in FIG. 2E.

The method and system are comprised of one-dimensional (1D) (A-line) OCT data (y-axis) displayed over time (x-axis) to create and present a real-time, scrolling, pseudo-3D (M-scan) OCT image (referred to herein as “depth-scans”) and corresponding video otoscopy images (FIG. 3A). In normal, healthy ears, the middle ear contains only air and therefore has no OCT signal (i.e. black only), as seen in FIG. 3A. In ears with clear, watery serous effusion (i.e. OME), heterogeneous, low-brightness scattering OCT signal is seen due to sparse effusion contents (e.g. dead middle ear epithelial cells) producing sparse OCT signal. With chronic or recurrent effusion, build-up of cellular secretions (e.g. proteins) due to immune cell function and/or epithelial remodeling results in mucoid effusion with increased scattering OCT signal. And in ears with cloudy, purulent (i.e. AOM) effusion present, homogeneous, high-brightness scattering OCT signal is seen due to increased turbidity from dense effusion contents (e.g. offending bacteria and responding immune system cells, resulting in pus) and thereby increased scattering OCT signal. While there is general aggregation of these OCT image qualities, there is a continuum of the contents present in MEEs and resulting OCT scattering brightness and signal density can range between the above two descriptions for OME and AOM depending upon the amount and type of MEE contents. As shown in FIG. 3A, in normal, healthy ears (left), this space contains only air (green arrows), but in abnormal ears, fluid can build up and the ability to differentiate this fluid as that of OME, wherein clear, watery serous effusion (orange arrow) is present, as shown in FIG. 3B, vs. that of AOM, wherein cloudy, purulent effusion (red arrow) is present, as shown in FIG. 3C, is important for decision-making around use of antimicrobials and/or TTP surgery. These images illustrate the OCT system and scope ability to assess the contents of the middle ear, even in ears with significant earwax present.

In one embodiment, the method and system comprise multiple modalities along with computational algorithms to provide diagnosis of otitis media. The computational algorithms comprise machine learning models, according to one embodiment. The method comprises applying machine learning models, using the OCT depth-scans, to guide identification and classification of No MEE vs. MEE with accuracy between about 87 to about 90%. In one embodiment, the depth-scans include a diagnostic quality, wherein the diagnostic quality includes a depth-scan signal from the TM and underlying middle ear space can be seen in the upper two-thirds of the depth-scan frame. In another embodiment, the depth-scan machine learning model identifies Serous effusion or classifies as No MEE. Serous effusion and No MEE are both clinically managed via “watchful waiting” instead of antimicrobial prescription. The method accurately identifies episodes of OME to identify chronic serous effusion and intervene with TTP, if appropriate. The novel multimodal machine learning approach that combines the depth-scan modality and the otoscopy modality synergistically accomplish tasks that either modality is not able to accomplish on its own. While there may be redundant information across modalities, there are clear examples where the two modalities provide orthogonal information that can influence diagnosis. For example, a depth-scan cannot be used to reliably detect a bulging TM, whereas this feature can often be identified in otoscopy. Conversely, depth-scans can be used to identify and quantify MEE turbidity, even in the presence of significant cerumen (earwax) obstruction of otoscopy view. While depth-scan near-infrared light cannot image through thick cerumen, the OCT system and scope operator only needs to aim the crosshairs through a small opening in the cerumen (ear canals are rarely 100% impacted) to obtain depth-scans of the middle ear. In one embodiment, the OCT system and scope images the middle ear contents even in ears with up to 94% obstruction by cerumen (e.g. FIG. 3A). In sharp contrast, otoscopy alone becomes increasingly difficult with cerumen obstruction of view, and cerumen removal is not commonly performed on children with AOM (29%), as performing otoscopy on an already agitated child is challenging enough. The multimodal neural networks comprise applying correlated otoscopy and depth-scan images for middle ear diagnosis.

In one embodiment, human MEE samples from pediatric subjects undergoing TTP surgery were used for ex vivo imaging and analysis. As shown in FIGS. 4A-4B, an ear model 200 with porcine intestinal lining is used as biomechanically and optically equivalent to that of the human TM. This TM-mimicking tissue paired with a commercial middle ear cavity used for otoscopy training (Nasco, as shown FIG. 4A) creates an equivalent middle ear model 210 for the OCT system and scope 100 imaging, as shown FIG. 4B. Placing the collected human MEE samples into the middle ear model provided a controlled means for collecting sufficiently large and diverse yet pathologically representative OCT system and scope depth-scan datasets.

In one embodiment, while varying the incident angle of the imaging beam to the TM, three recordings were taken for a device maximum duration of 100 seconds for each sample. The OCT system and scope generates 38 A-lines per second; therefore, each MEE sample produced at least 11,400 A-lines of data in total. The MEE samples were then quantitatively processed to determine turbidity and viscosity using a spectrophotometer (Thermo Fisher Scientific) and viscometer (RheoSense), respectively. These quantitative measurements were used to verify and substantiate the collaborating otolaryngology surgeons' MEE classifications. The ear model with the TM only (no MEE) was also imaged to simulate normal, healthy ears. The resulting data consists of 47 "No MEE" samples and 47 MEE samples: 8 "Serous" samples (OME) and 39 "Mucoid" samples. F1 scores were used in analysis to offset impact due to the significantly fewer number of Serous samples.

Figure 5:
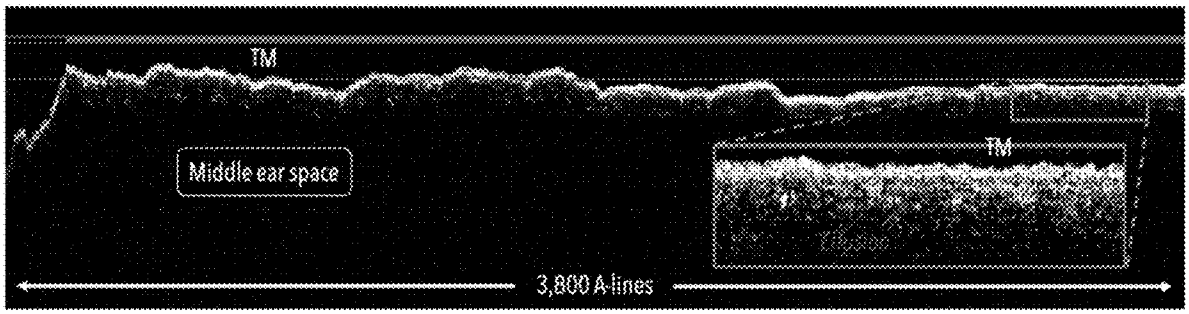
FIG. 5 is an annotated depth-scan with the dense, horizontal, white signal trace represents the tympanic membrane (TM; eardrum) and the scattering below the line indicates the presence of effusion (shown in more detail in the inset). Quality depth-scan data segments were annotated with a colored line across the top of the images. Annotations were color coded based on clinical classification, confirmed by lab analysis, with red (shown) indicating Mucoid effusion.

In the depth-scans, the signal from the biomimetic TM varied in depth position due to motion during imaging, which was done intentionally to simulate natural clinical data collection motion from both the patient and the OCT system and scope operator. As part of image preprocessing, the depth location of the TM is identified by finding the maximum intensity value per A-line and shifted each individual A-line so that the TM aligned at the top of the image. Each depth-scan was manually annotated by an unbiased OCT expert based on the presence and clarity of TM signal in each A-line, as shown FIG. 5. To account for the fact that it is unlikely a single A-line would be sufficient to yield a reliable diagnosis, each depth-scan was separated into groups of twelve A-lines for use as inputs to the models.

The depth-scans of the three different classes (No MEE, Serous, and Mucoid) visually appeared to differ primarily in the signal scattering beneath the TM. The No MEE class showed absence of signal beneath the TM while the two MEE classes differed in the degree of brightness and density of signal beneath the TM, with the Mucoid class having brighter and higher density of signal. This is consistent with previously published clinical data.

Figure 6:
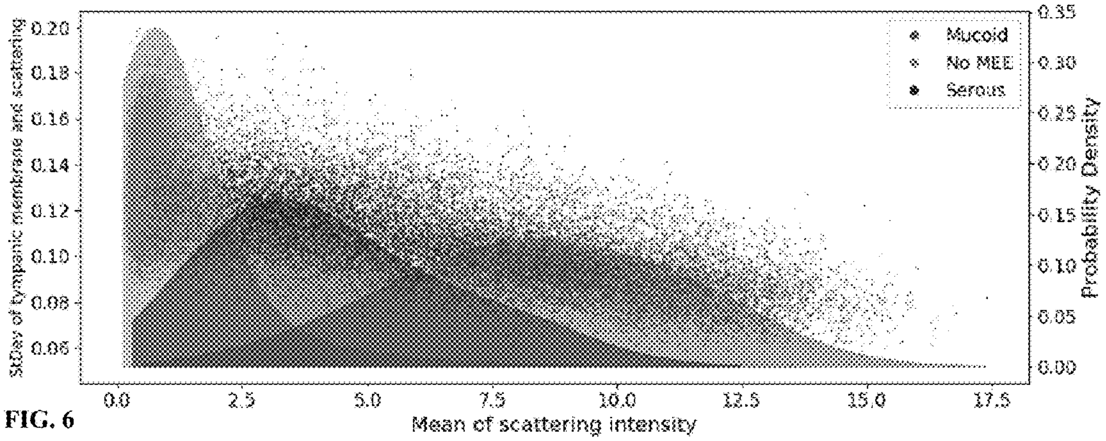
FIG. 6 is a scatter plot (with probability density) of two features selected for use in the support vector machine (SVM) in each of the three classes and there exists a reasonable amount of separation between the Mucoid class and No MEE classes, but the Serous and No MEE classes have the largest area of overlap, which could account for the higher misclassification rate of Serous samples.

For analysis, the method comprises 3 features from the depth-scans including: (1) average intensity of the scattering beneath the TM, (2) standard deviation of pixel intensity across the TM and underlying middle ear space, and (3) ratio of the sum of pixel intensity of the TM to the sum of pixel intensity of the middle ear space. In one embodiment, a support vector machine (SVM) is used, which is a model suitable for this classification task using the three features from the depth scans, and also trained a Central Neural Network (CNN), a machine learning model that does not require the three features. The dataset is separated into a training partition (~80%), a validation partition (~10%), and a testing (~10%) partition. To avoid data leakage, the partitions are split on the sample level, i.e. all OCT system and scope data acquisitions performed on a sample would be in the same partition. Stratified k-fold cross validation (k=5) was performed to rule out the possibility of picking an easy testing partition by chance and no significant difference between the folds was found. For the 3 features, the SVM shows a reasonable amount of separation between the Mucoid vs. No MEE classes. The Serous class has overlap with both of the other classes, more so with No MEE, as shown in FIG. 6.

Figure 7A:
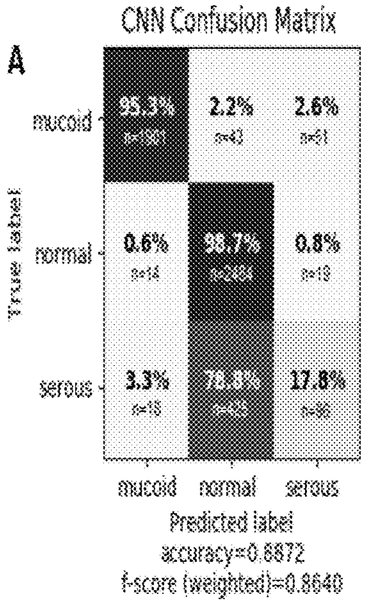
FIG. 7A is a confusion matrix of Central Neural Network (CNN) predictions on the test partition. High Mucoid and No MEE recall values indicate promising results. The misclassification of Serous samples as No MEE can be attributed to the close similarity of the depth scans typical of those classes (i.e. low brightness and density of signal for Serous vs. no signal for No MEE).
Figure 7B:
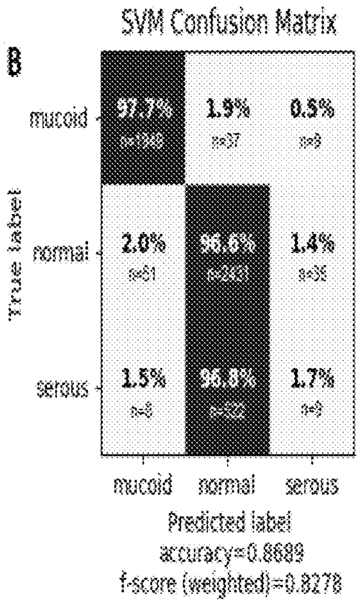
FIG. 7B is a confusion matrix of multiclass SVM predictions on the test partition. Similar to the CNN, the SVM excels at differentiating Mucoid samples, but struggles to correctly identify Serous samples.
Figure 7C:
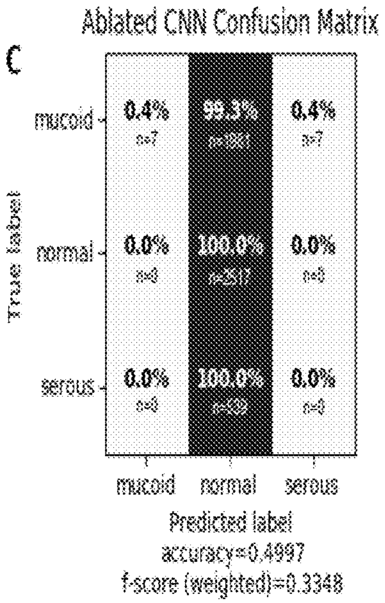
FIG. 7C is a confusion matrix of CNN predictions from an ablation study sample set wherein the area beneath the TM was ablated (values=0). Results demonstrate that the presence of depth-scan scattering beneath the TM (i.e. middle ear space) significantly and appropriately influences the CNN's classification of the sample, as expected.

As shown in FIGS. 7A-7C, the CNN performed similarly, albeit slightly better than the SVM. Both the CNN and SVM excel at identifying Mucoid and No MEE samples (F1-scores: CNN: 96.79% Mucoid, 90.84% No MEE; SVM: 97.38% Mucoid, 88.29% No MEE). However, both models struggle with accurately discriminating Serous from the other two classes. To evaluate this, a multi-step SVM model comprising two binary SVMs: (1) No MEE vs. MEE and (2) Mucoid vs. Serous. This model performed comparably to the multiclass SVM (F1-scores: 97.16% Mucoid, 88.33% No MEE; 87.43% No MEE vs. MEE accuracy, 92.67% Mucoid vs. Serous accuracy). Compared to publications, these values are: (1) comparable to the ~90% accuracy for subjective blinded reader analysis and classification of OCT images as No MEE, Serous effusion (e.g. OME), and Non-serous effusion (e.g. AOM and mucoid) and (2) higher than the ~50% accuracy for subjective blinded reader analysis and classification of standard otoscopy image.

To verify that CNN is using reasonable parts of the depth-scans for image classification, an ablation study was performed by removing pixels from various areas of the depth-scans. When the signal underneath the TM was ablated (values=0), the model is unable to discriminate between No MEE and MEE samples, as expected. As shown in FIG. 7C, the results show that the signal below the TM (i.e. middle ear) has the most influence on CNN classification of depth-scans, which is appropriate and in-line with OCT expert analysis technique for evaluating depth-scans.

The overall strong performance of the SVM trained on simple hand-engineered features and CNN indicates the OCT system and scope is a modality with intrinsically high diagnostic potential to improve user diagnostic accuracy. While the CNN slightly outperformed the SVM, this gap widen with the additional data collected, and therefore will proceed with the CNN. Though the performance of the SVM and CNN models support the hypothesis that use of such models in the OCT system and scope facilitate superior diagnostic accuracy for detection of No MEE and Mucoid effusion, accurate diagnosis of OME (i.e. Serous effusion) requires further development. The method comprises incorporation of otoscopy images into a novel multimodal machine learning model to achieve superior classification performance. Furthermore, conducting the proposed clinical study in a pediatric primary care setting is essential to collect data from patients with Purulent effusion, rarely seen at the time of TTP surgery. The higher turbidity due to increased density of fluid contents results in increased scattering signal from ears with AOM (purulent) depth-scans, beyond that of Mucoid effusion.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The goal of these Examples is to illustrate development and evaluation of a novel multimodal imaging machine learning approach to achieve reliable ease of quality data collection and accurate, assisted interpretation of the OCT system and scope images (otoscopy and depth-scans), regardless of user expertise. Such development could result in a robust CNN model suitable for clinical deployment to evaluate impact on diagnostic accuracy and clinical outcomes focused on, ultimately, effective treatment planning for restoring ear health.

Example 1: Reliable Usability of an OCT System and Scope by Guiding Image Capture Using a Deep Learning Model OCT System and Scope Software The OCT system and scope can improve the standard of care only if the clinicians of a variety of otoscopy expertise levels are able to easily and reliably collect quality data within their existing workflow. The primary difference between using the OCT system and scope and a standard otoscope to perform a patient exam is that the user must be more cognizant of aiming. For the OCT system and scope, a crosshair is displayed at the center of the otoscopy field-of-view (see FIG. 4A) to indicate the location where the depth-scan is being acquired. Deep learning methods to develop and test software capable of real-time marking of the TM as a target region of interest (ROI) to facilitate easier aiming and diagnostic quality data capture, as well as fast utility.

Experimental Design and Methods

Data Annotation for Model Training

Labeled data from Example 1 will be used for developing and training the model for auto-detection of the ROI. Data annotation for Example 2 would involve defining a mask that demarcates the TM from the rest of the otoscopy image. Manual annotation of the TM by an otoscopy expert for every video otoscopy frame will be cost and timeline prohibitive, so two semi-automated methods are used. The active contour algorithm can be used to expedite annotations by automatically fine tuning a rough manual outline similar to a smart selection tool in an image editor application. Additionally, segmentation network is trained on manual annotations and run the model on unannotated data. Therefore, the expert will only need to accept or modify segmentation suggestions instead of manually drawing the entire annotation. This iterative technique is interactive segmentation.

Figure 9:
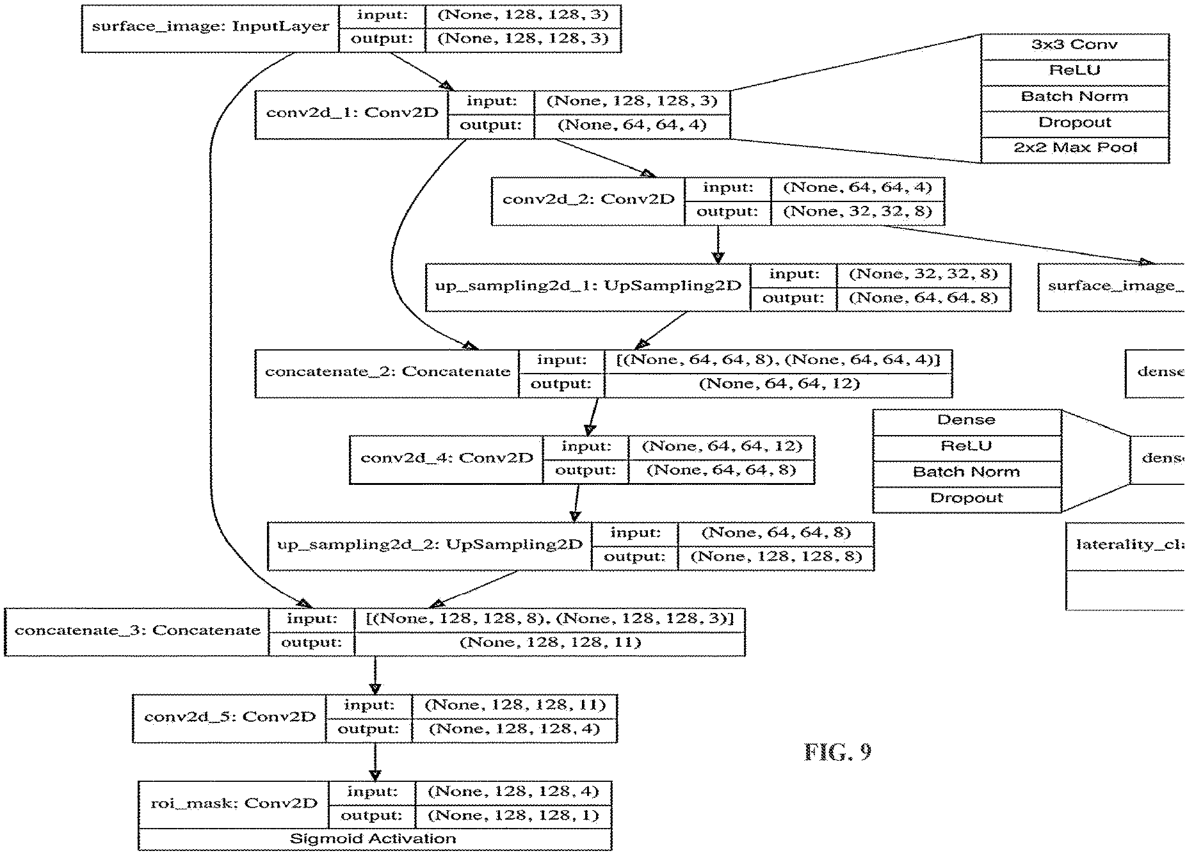
FIG. 9 is a schematic flow chart of the architecture of the multimodal CNN to facilitate both: (1) ease and reliability of quality data capture from the OCT system and scope users with a range of otoscopy expertise, and (2) easy and reliable interpretation of OCT system and scope images for classifying No MEE, OME, and AOM. To accomplish this, the ROI segmentation algorithm (green) evaluates the otoscopy image data and enables real-time overlay of the ROI in the otoscopy display.
Figure 9:
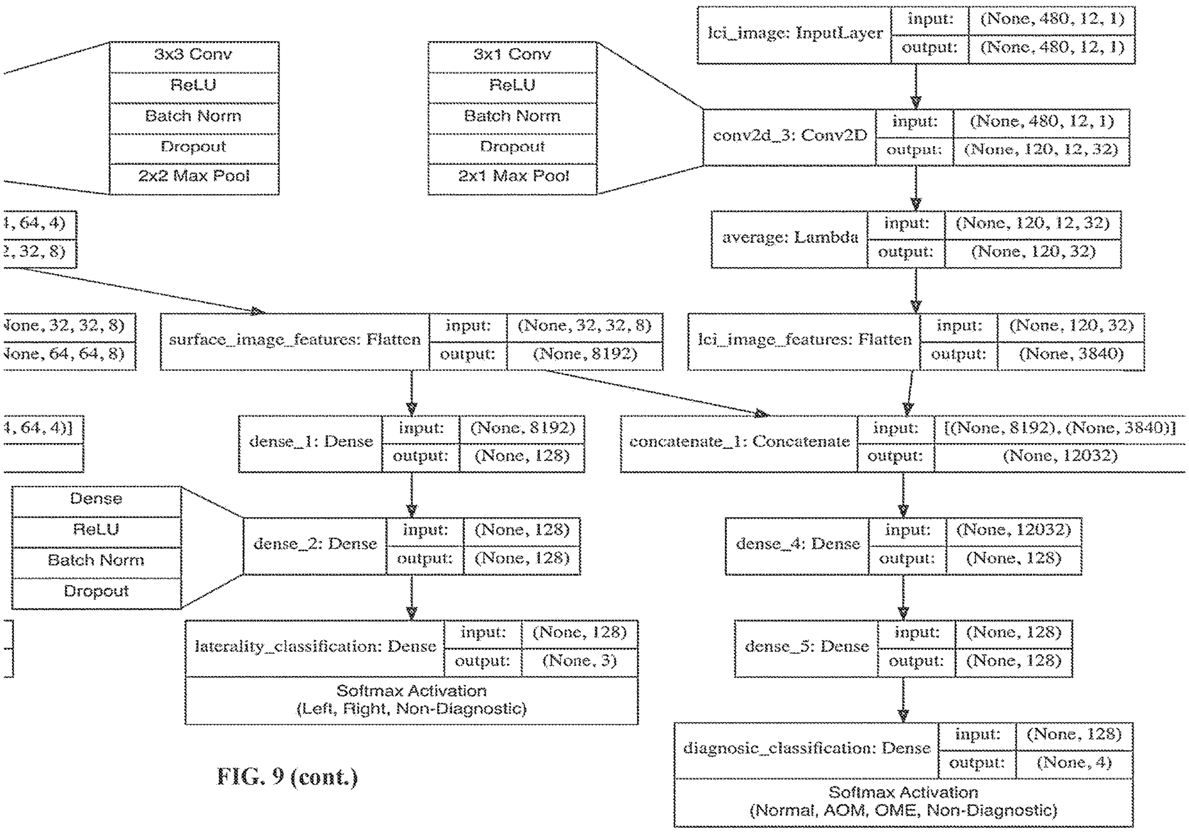

Region of Interest Segmentation Algorithm and Integration With Deep Learning OCT System and Scope Software As shown in FIG. 9, the proposed architecture of this deep network takes into account both Example 2 and Example 3 objectives while also considering the resulting OCT system and scope software implementation. The layers are divided into two stages, an encoder stage and a decoder stage. The encoder stage comprises an Alex-net type structure that converts the input otoscopy image into features. The decoder stage then up-samples these features into the target mask through a series of learned up-sampling layers combined with skip connections. The loss function shall be the Dice loss and the network shall be optimized using the Adam optimizer. The remaining architecture details are discussed in Example 3. Based on this information, the resulting Deep Learning OCT system and scope software can draw an outline of the target mask over the otoscopy image in real-time to facilitate a real-time imaging target for the OCT system and scope operator to aim the crosshair. The architecture comes from the evidence that suggests combining segmentation and classification tasks into a single network improves both segmentation and classification performance compared to separate networks. Furthermore, the otoscopy (green, red) and depth-scan data (blue) are evaluated and classified (brown) into one of the three diagnostic classes.

Python and TensorFlow 2.0 or later is used as the deep learning software stack. The model will be trained using consumer grade Nvidia graphics cards on a solid-state drive backed Ubuntu workstation using the latest CUDA and cuDNN libraries. About 80% of the acquired data is used for training, 10% of the acquired data is used for refinement of the model and hyperparameters, and 10% of the acquired date is used for testing. The segmentation masks generated from the model will be compared with user generated segmentation masks for pixel-by-pixel accuracy. Integration of the model developed in Python with the C++ based application will be done using TensorFlow lite libraries to generate portable model files that can be trained on a desktop computer and executed on embedded systems, such as that internal to the OCT system and scope. Initial prototyping estimates that each forward pass will consume ~9 million floating point multiplications additions. Real time operation at 30 frames per second therefore requires ~270 million floating point multiply adds per second. This computational load is within the theoretical capability of the existing OCT system and scope hardware with a total estimated CPU throughput of 1 billion FLOPS per core.

Clinical User Testing and Development of OCT System and Scope With Deep Learning OCT System and Scope Software Usability Upgrade Using data from a large number of multimodal ear images, the initial Deep Learning OCT system and scope software usability upgrade will be developed and integrated into the clinical OCT system and scope devices via software upgrade. The OCT system and scope with and without use of Deep Learning OCT system and scope software guidance with a user group consisting of: primary care physicians, physician assistants, and nurse practitioners. The clinical team members will be given a brief tutorial and training practice session to use the OCT system and scope with this new mode of operation. Each clinical user will collect data on 10 patients total, 5 with and 5 without Deep Learning OCT system and scope software. The impact of Deep Learning OCT system and scope software is analyzed using the following quantitative metrics: 1) User experience through a brief quantitative survey following the ear examination, as well as a focus group at the end to more broadly discuss; 2) Calculation of intra- and inter-user quality data collection rate; and 3) Time duration required to achieve quality data collection from first insertion of the probe into the ear canal via analysis of the otoscopy videos.

Once all Year 2 clinical data is collected and annotated, the model will be trained, refined, and tested on the complete clinical dataset (80/10/10 split respectively). The model will then be implemented into the OCT system and scope software and clinical user testing results and feedback will drive Deep Learning OCT system and scope software usability design features.

Data Analysis and Interpretation

Data analysis and testing will be performed on 3 key steps: (a) Deep Learning OCT system and scope software model development for segmentation, (b) implementation and integration with the OCT system and Scope software, and (c) iterative performance testing in the clinical setting. The segmentation accuracy for the CNN will be calculated using the Dice score and compared to gold standard annotations. Clinical performance will be evaluated using the 3 metrics defined above. A score for each metric will be separately assigned, and differences in the score with and without Deep Learning OCT system and scope software will be recorded.

Alternative Approaches

An alternative option is using different network architectures particularly those where segmentation and classification is done separately. Also, if the proposed network becomes too computationally expensive for existing OCT system and Scope hardware while implemented with all other operations in the system, an alternative approach would be to use a different neural network architecture designed for computational efficiency, starting with SD-Unet101. In addition, the onboard GPU can be used for another 16 billion FLOPS and deep neural networks are excellent candidates for GPU acceleration.

Enhance usability of the device as measured by: (1) quantitative user experience survey and focus group feedback, (2) intra- and inter-user quality data collection rate, and (3) time to quality data collection from first insertion of the probe into the ear canal via analysis of the otoscopy videos. An improvement in each of these metrics by at least 20% is expected.

Example 2: A Multimodal Deep Learning Model to Provide Diagnostic Assistance Using an OCT System and Scope and Resulting Otoscopy and Depth-Scan Data The use of CAD, specifically machine learning algorithms, for the OCT system and Scope is intended to enhance diagnostic ability for all users. Such machine assistance becomes particularly valuable in a multi-modality setting, like the OCT system and Scope, which has both otoscopy and depth-scan images. Building upon the successful model developed previously using ex vivo human MEE imaged in ear phantom models, as well as the otoscopy classification work developed, the CNN will be trained using in vivo clinical data to classify a group of A-lines and corresponding otoscopy image, into classes that provide a different disease management path.

Multimodal OCT system and Scope data (otoscopy and depth-scan images) will be used for three-way classification to ultimately aid diagnosis. The following data augmentation techniques to the otoscopy images will be employed: add noise, horizontal and vertical scaling, horizontal mirroring (with care to adjust the laterality label), brightness and contrast adjustment, rotation, and circular cropping to simulate different ear speculum sizes. The following data augmentation techniques to the depth-scans will be employed: adding noise, vertical and horizontal scaling, brightness and contrast adjustment. In addition to data augmentation, as done previously, the depth-scans are preprocessed in the following ways: intensity normalization and TM position normalization to place maximum intensity signal of each A-line at the top of the image.

Figure 8A:
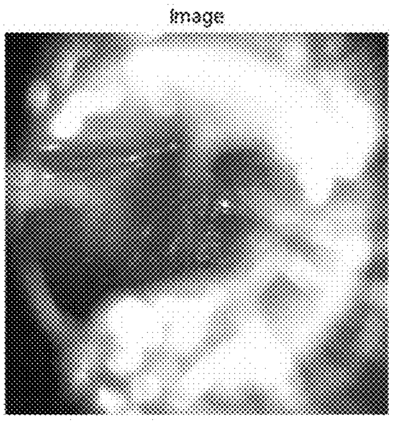
FIGS. 8A-8C are photographs from the otoscope showing the Results on segmentation of otoscopy using multilayer U-net, where
Figure 8B:
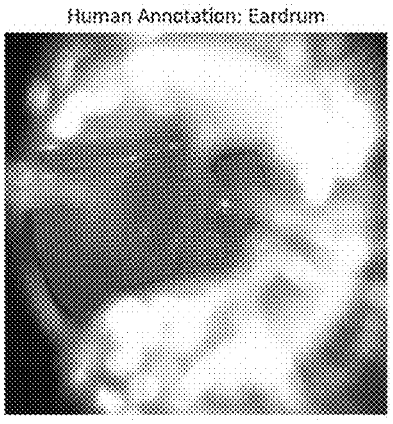
Figure 8C:

Image Classification Algorithm and Integration With OCT System and Scope Software Example 3 uses features generated by the encoder portion of the U-net described in Example 2. FIGS. 8A-8C are photographs from the otoscope showing the Results on segmentation of otoscopy using multilayer U-net, where FIG. 8A is the original otoscopic image; FIG. 8B is the human annotation of the eardrum; and FIG. 8C is the AI annotation of the eardrum with a dice score of 0.96. Dice score is commonly used for manually annotated and machine segmented examples. Basic structure used for segmentation comprises the U-net architecture and in one specific case included 6 layers with convolution, pooling and spatial dropout in both encoder and decoder arms of U-net architecture.

These features are derived from the otoscopy image and may be combined with the features derived from the depth-scan classification network. The classification network consists of multiple 3×1 convolution, batch normalization, dropout, and 2×1 max pooling operations. These operations extract features from individual A-lines. Features from multiple A-lines are then averaged together before being concatenated with features derived from the otoscopy image segmentation U-net and then fed into a classification head. The combined features allow the multi-class classification layers to use information from both otoscopy and depth-scan images for the classification task. Using the same encoder network for both segmentation and classification tasks improves computational efficiency and improves generalizability. The algorithm development tools will be identical to those described in Example 2. Each forward pass through the classification neural network by itself consumes about 1 million floating point multiply addition operations, corresponding to 30 million operations per second for the OCT system and Scope line rate of 30 Hz.

The results from the model will be compared with those from validated otoscopists and OCT experts to estimate the accuracy of the model. These values will also be compared to results seen from clinical datasets generated with the OCT system and Scope when analyzed by clinicians in previous studies, previous results from the otoscopy classification algorithms, and published clinical statistics produced with the use of other medical devices and diagnostic techniques. The method will quantitatively prove superior diagnostic capabilities with the OCT system and Scope when paired with the use of machine learning (≥90% accuracy for identification of MEE and ≥80% accuracy for classification of OME or AOM) over that of traditional otoscopy, pneumatic otoscopy, or tympanometry.

Develop a CNN model for classification of OCT system and Scope data (otoscopy and depth-scans), using 80% of Example 1 data for training, 10% for hyperparameter optimization, and 10% for testing, to achieve: ≥90% accuracy for classifying MEE vs. No MEE; ≥80% accuracy for classifying AOM vs. OME.

CONCLUSION

The system and method described above comprise (1) Deep Learning OCT system and scope software, a deep learning approach to improve OCT system and scope ease of reliable quality data collection, regardless of user otoscopy expertise, and (2) a robust CNN capable of correctly identifying the presence/absence of MEE, as well as classification, superior to that reported for the current clinical standard-of-care technologies: basic otoscopy, pneumatic otoscopy, or tympanometry.

Example: Machine Learning Data

Subjects

Pediatric patients (4 years old or under) scheduled for office visits with ear related complaints.

Location

University of Pittsburgh Medical Center—Children's Hospital

Data Collection

Following informed consent, pediatric subjects are bilaterally imaged (both ears) by the attending clinician with the OtoSight Middle Ear Scope, and corresponding clinical and diagnostic data is recorded via electronic database forms for later image classification for machine learning development and analysis.

Figures 10A, 10B:
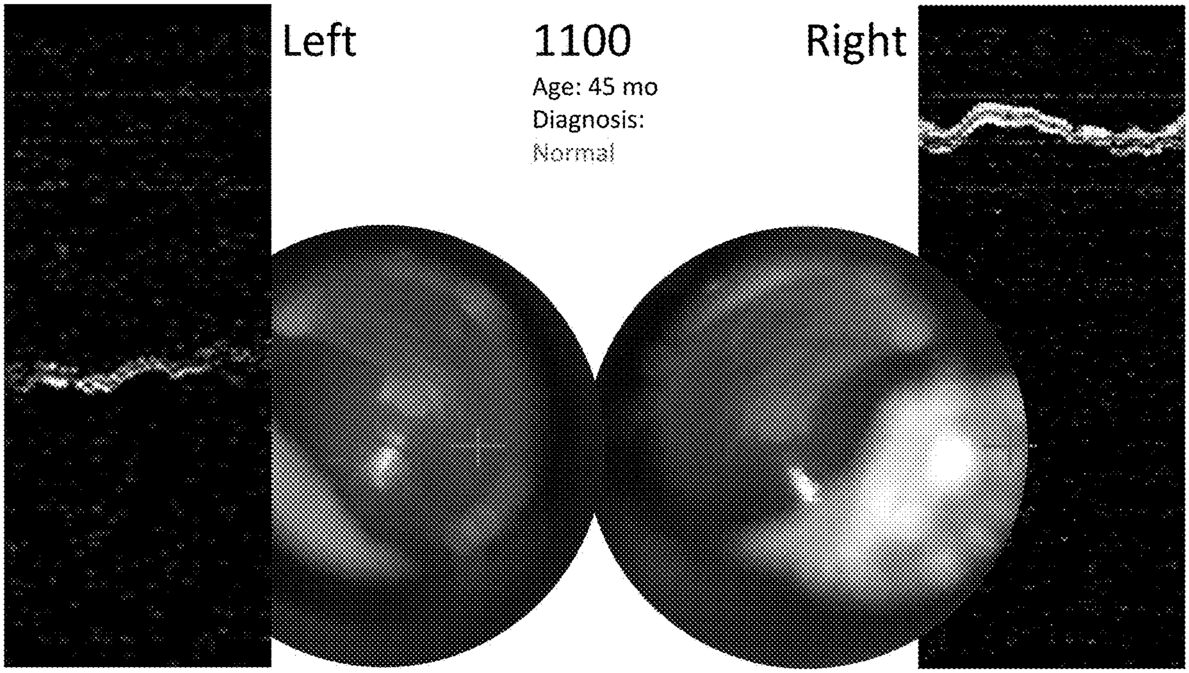
FIG. 10A are OCT images and otoscope images of the left ear and FIG. 10B are OCT images and otoscopic images of the right ear of a 45 month old subject showing normal or healthy TM.
Figures 11A, 11B:
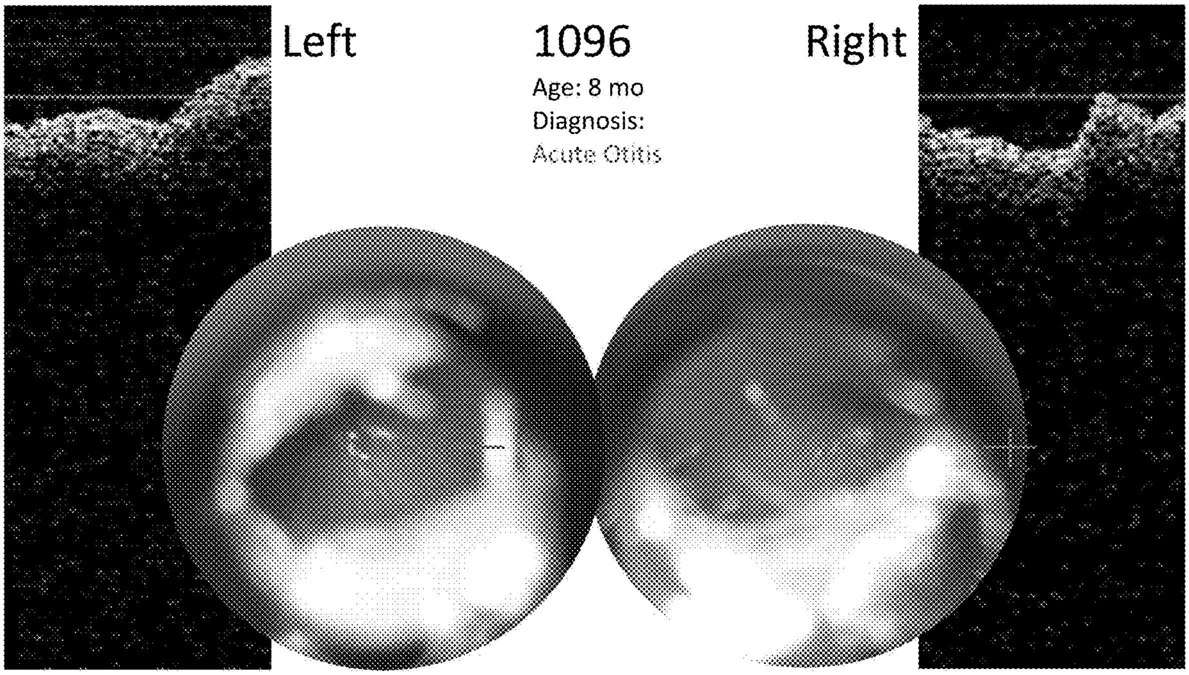
FIG. 11A are OCT images and otoscope images of the left ear and FIG. 11B are OCT images and otoscopic images of the right ear of an 8 month old subject showing acute otitis.

FIG. 10A are OCT images and otoscope images of the left ear and FIG. 10B are OCT images and otoscopic images of the right ear of a 45 month old subject showing normal or healthy TM. FIG. 11A are OCT images and otoscope images of the left ear and FIG. 11B are OCT images and otoscopic images of the right ear of an 8 month old subject showing acute otitis. The machine learning algorithm was able to accurately identify acute otitis from the OCT images as correlated with the otoscope images diagnosed by a doctor.

System

As used above, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

Software includes applications and algorithms. Software may be implemented in a smart phone, tablet, or personal computer, in the cloud, on a wearable device, or other computing or processing device. Software may include logs, journals, tables, games, recordings, communications, SMS messages, Web sites, charts, interactive tools, social networks, VOIP (Voice Over Internet Protocol), e-mails, and videos.

In some embodiments, some or all of the functions or process(es) described herein and performed by a computer program that is formed from computer readable program code and that is embodied in a computer readable medium. The phrase "computer readable program code" includes any type of computer code, including source code, object code, executable code, firmware, software, etc. The phrase "computer readable medium" includes any type of medium capable of being accessed by a computer, such as read only memory (ROM), random access memory (RAM), a hard disk drive, a compact disc (CD), a digital video disc (DVD), or any other type of memory.

All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A system for diagnosing otitis media comprising: a method for observing contents behind the eardrum and generating data from the contents behind the eardrum, a method for observing the surface of the eardrum and generating images of the surface of the eardrum, and a computation method jointly using the data from the contents behind the eardrum and data from the images of the surface of the eardrum to provide a diagnosis of otitis media, wherein the computational method uses multimodal Convolutional Neural Network (CNN) that jointly processes data from the images and data from behind the eardrum through parallel encoder branches; wherein the computational method for diagnosing otitis media segments the eardrum from the rest of the contents; wherein the method for observing contents behind the eardrum generates a surface image of the eardrum that is co-registered with subsurface depth-scan data in spatial coordinates, wherein the surface image and the subsurface depth-scan data are acquired simultaneously by an OCT system and scope device.

2. The system of claim 1, wherein the method for observing the contents behind the eardrum uses electromagnetic radiation, low-coherence interferometry, or mechanical waves.

3. The system of claim 1, wherein the method for observing the eardrum surface uses electromagnetic radiation and an electromagnetic detector.

4. The system of claim 1, wherein the computation method for diagnosing otitis media is based on machine learning including deep learning, neural networks, support vector machines, logistic regression, or random forests.

5. The system of claim 1, wherein only the subsurface information is used to detect contents and structures in the middle ear.

6. The system of claim 5, wherein the computational method provides a scale that indicates state of the middle ear from healthy to severely ill, including No MEE, OME and AOM.

7. The system of claim 6, further comprising diagnosing the type of fluid present behind the eardrum, wherein the type of fluid includes serous, mucoid, mucopurulent, or seropurulent.

8. A method for diagnosing otitis media comprising: observing contents behind the eardrum and generating data from the contents behind the eardrum, observing the surface of the eardrum and generating images of the surface of the eardrum, and jointly using the data from the contents behind the eardrum and data from the images of the surface of the eardrum to provide a diagnosis of otitis media through a computational method, wherein the computational method uses multimodal Convolutional Neural Network (CNN) that jointly processes data from the images and data from behind the eardrum through parallel encoder branches; wherein the computation method for diagnosing otitis media is based on machine learning including deep learning, neural networks, support vector machines, logistic regression, or random forests; wherein the computational method for diagnosing otitis media segments the eardrum from the rest of the contents; wherein the observing contents behind the eardrum generates a surface image of the eardrum that is co-registered with subsurface depth-scan data in spatial coordinates, wherein the surface image and the subsurface depth-scan data are acquired simultaneously by an OCT system and scope device.

9. The method of claim 8, wherein the observing the contents behind the eardrum uses electromagnetic radiation, low-coherence interferometry, or mechanical waves.

10. The method of claim 8, wherein the observing the eardrum surface uses electromagnetic radiation and an electromagnetic detector.

11. The method of claim 8, wherein only the subsurface information is used to detect contents and structures in the middle ear.

12. The method of claim 11, wherein the computational method provides a scale that indicates state of the middle ear from healthy to severely ill, including No MEE, OME and AOM.

13. The method of claim 12, further comprising diagnosing the type of fluid present behind the eardrum, wherein the type of fluid includes serous, mucoid, mucopurulent, or seropurulent.

* * * * *